(12) United States Patent
Potechin et al.

(10) Patent No.: US 7,297,667 B2
(45) Date of Patent: Nov. 20, 2007

(54) LIQUID CLEANSING COMPOSITIONS

(75) Inventors: Kathy Potechin, Short Hills, NJ (US); Peter Haugk, Lincoln Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 173 days.

(21) Appl. No.: 11/185,360

(22) Filed: Jul. 20, 2005

(65) Prior Publication Data

US 2006/0019861 A1 Jan. 26, 2006

Related U.S. Application Data

(60) Provisional application No. 60/589,304, filed on Jul. 20, 2004.

(51) Int. Cl.
*C11D 1/02* (2006.01)
*C11D 1/88* (2006.01)
*C11D 3/22* (2006.01)
*C11D 3/37* (2006.01)
*A61K 8/73* (2006.01)

(52) U.S. Cl. ............ 510/151; 510/138; 510/159; 510/414; 510/426; 510/433; 510/434; 510/474; 510/475; 510/490; 510/499; 424/401; 424/70.16; 424/70.21; 424/70.22

(58) Field of Classification Search ............ 510/138, 510/151, 159, 414, 426, 433, 434, 474, 475, 510/490, 499; 424/401, 70.16, 70.21, 70.22
See application file for complete search history.

(56) References Cited

U.S. PATENT DOCUMENTS

| 5,030,374 | A | 7/1991 | Tranner |
| 6,033,680 | A | 3/2000 | Dixon et al. |
| 6,533,873 | B1 | 3/2003 | Margosiak et al. |
| 6,635,702 | B1 | 10/2003 | Schmucker-Castner et al. |
| 6,642,198 | B2 | 11/2003 | Pflederer et al. |
| 6,846,785 | B2 | 1/2005 | Patel |
| 2002/0123438 | A1 | 9/2002 | Pflederer et al. |

FOREIGN PATENT DOCUMENTS

| EP | 1364639 | 11/2003 |
| GB | 2290551 | 1/1996 |
| GB | 2297762 | 8/1996 |
| WO | WO91/14421 | 10/1991 |

OTHER PUBLICATIONS

Glucam™ E-10 Methyl Glucoside Derivative Technical Data Sheet. Noveon. Aug. 1, 2005.
Glucam™ E-20 Methyl Glucoside Derivative Technical Data Sheet. Noveon. Aug. 1, 2005.
Glucam™ P-10 Methyl Glucoside Derivative Technical Data Sheet. Noveon. Aug. 1, 2005.
Glucam™ P-20 Methyl Glucoside Derivative Technical Data Sheet. Noveon. Aug. 1, 2005.
Glucamate™ DOE-120 Methyl Glucoside Thickener Technical Data Sheet. Noveon. Jul. 14, 2006.
Glucamate™ LT Methyl Glucoside Derivative Technical Data Sheet. Noveon. Jul. 14, 2006.
Noveon Carbopol® Aqua SF-1 Polymer Summary Sheet CP-29, Nov. 2002.
Noveon Carbopol® Aqua SF-1 Polymer Technical Data Sheet TDS-294, Jul. 2003.
3V Synthalen W2000 Cosmetic Technical Report No. 6—Edition 4, no date given.

*Primary Examiner*—Brian Mruk
(74) *Attorney, Agent, or Firm*—Michael F. Morgan

(57) ABSTRACT

Novel cleansing compositions and methods for making same are described. Preferred embodiments provide compositions comprising an acrylate copolymer, an alkoxylated methyl glucoside polyol, and a surfactant. Preferred alkoxylated methyl glucoside polyols among those useful herein may include ethoxylated and/or propoxylated methyl glucoside polyols.

19 Claims, No Drawings

LIQUID CLEANSING COMPOSITIONS

CROSS-REFERENCE TO RELATED APPLICATIONS

This application claims benefit of U.S. Provisional Application No. 60/589,304, filed Jul. 20, 2004, the disclosure of which is hereby incorporated by reference herein in its entirety.

BACKGROUND OF THE INVENTION

While cleansing compositions comprising various surfactants and structuring agents, such as, for example, acrylate copolymers, have been described (e.g., U.S. Pat. No. 6,635,702 B1, U.S. Pat. No. 6,642,198), it has been found that the use of anionic and amphoteric surfactants in combination with acrylate copolymers do not always provide desired characteristics, such as sufficient foam. Acrylate copolymer in cleansing systems can inhibit foaming with use of typical surfactants, such as sodium laureth sulfate and cocamidopropyl betaine.

BRIEF SUMMARY OF THE INVENTION

The present invention is directed, in part, to novel cleansing compositions and methods for making same. Specifically, in certain embodiments, there are provided compositions comprising an acrylate copolymer, an alkoxylated methyl glucoside polyol, and a surfactant. Another embodiment of the invention relates to methods for making cleansing compositions.

DETAILED DESCRIPTION OF THE INVENTION

In certain embodiments, the invention is directed to cleansing compositions that are structured liquids that provide improved foaming, excellent skin feel, and/or good viscosity/rheological profiles for dispensing and the ability to suspend other additives. In certain embodiments, the compositions of the invention are non-emulsion liquid cleansing compositions.

In certain embodiments, the present invention is directed to cleansing compositions comprising at least one alkoxylated methyl glucoside polyol and at least one acrylate copolymer. Preferably, the methyl glucoside is alkoxylated with ethylene or propylene oxide.

According to one embodiment of the present invention, a composition is provided comprising an alkoxylated methyl glucoside polyol, an acrylate copolymer and at least one surfactant. In certain embodiments of the invention, the surfactant comprises an anionic surfactant. In certain embodiments of the invention, the surfactant comprises an amphoteric surfactant. In certain embodiments of the invention, the composition comprises both an anionic surfactant and an amphoteric surfactant.

In certain embodiments of the invention, the anionic surfactant is preferably present in an amount of about 3% to about 25% by weight of the total composition, about 5% to about 18%, or about 7% to about 12% (all by weight of the total composition).

In certain embodiments of the invention, the amphoteric surfactant is preferably present in an amount of about 0.05% to about 15% by weight of the total composition, about 0.5% to about 10%, or about 1% to about 8% (all by weight of the total composition).

In certain embodiments of the invention, the acrylate copolymer is preferably present in an amount of about 0.1% to about 12% by weight of the total composition, about 0.5% to about 8%, or about 1% to about 5% (all by weight of the total composition).

In certain embodiments of the invention, the alkoxylated methyl glucoside polyol is preferably present in an amount of about 0.05% to about 6% by weight of the total composition, about 0.1% to about 4%, or about 0.2 to about 2% (all by weight of the total composition).

In certain embodiments, the alkoxylated methyl glucoside polyol is a methyl glucoside alkoxylated with ethylene or propylene oxide. In certain embodiments, mixtures of ethoxylated glucoside polyols and propoxylated glucoside polyols may be used. Preferably, the ethoxylated and/or propoxylated methyl glucoside is present in an amount of about 0.05% to about 6% by weight of the total composition, about 0.1% to about 4%, or about 0.2% to about 2% (all by weight of the total composition).

In certain embodiments, a basic neutralizing agent is preferably present in an amount of about 0.01% to about 5% by weight of the total composition, about 0.05% to about 4%, or about 0.1% to about 3% (all by weight of the total composition).

In certain embodiments, the composition of the invention additionally comprises water. The amount of water may vary, but may be up to about 99% by weight of the total composition, for example, about 35% to about 97%, or about 50% to about 90% (all by weight of the total composition).

In certain embodiments, the composition may further comprise effective amounts of optional ingredients including, but not limited to: colorants, fragrances, antibacterial, preservatives, antioxidants, beads, mica, glitter, opacifying agents, and pearlizing agents. In certain embodiments, the beads may comprise fragrance, exfoliating ingredients and/or moisturizing ingredients.

According to one preferred embodiment of the invention, the composition comprises beads containing shea butter. Preferably, the beads have a diameter in the range of about 100 to about 1200 microns.

In certain embodiments, the preferred pH of the composition is at least about 5.5, for example, about 6.0 to about 7.5, or about 6.4 to about 7.2.

Alkoxylated methyl glucoside polyols suitable for use in this invention include, without limitation, those having an average degree of alkoxylation of about 8 to about 22. Suitable alkoxylated methyl glucoside polyols include, but are not limited to, ethoxylated and propoxylated methyl glucosides. Examples include, but are not limited to, methyl gluceth-10, methyl gluceth-20, PPG-10 methyl glucose ether, and PPG-20 methyl glucose ether.

Examples of suitable anionic surfactants include, but are not limited to, alkyl sulfates, ethoxylated alkyl sulfates, alkyl sulfonates, alkyl olefin sulfonates, alkyl succinates, alkyl sulfosuccinates, alkyl ethoxy sulfosuccinates, acyl and alkyl glutamates, alkyl phosphates, alkyl ether carboxylates, alkyl isethionates, and acyl amides.

Suitable amphoteric surfactants may include, but are not limited to, betaine surfactants. Examples of suitable amphoteric surfactants include, but are not limited to, alkyl betaines, alkylamido betaines, alkyl sulfobetaines, alkyl sultaines and alkylamido sultaines. Preferably, the alkyl and acyl groups generally contain from about 8 to about 18 carbons.

Suitable acrylate copolymers include, without limitation, those described in U.S. Pat. No. 6,635,702 B1 (hereby incorporated by reference herein) and those selected from the group consisting of:

monomers or copolymers of one or more of methacrylic acid, acrylic acid, itaconic acid, esters of any of the foregoing and mixtures of any of the foregoing;

a member of group (a) copolymerized with one or more members selected from the group consisting of Steareth-20, Steareth-50, Ceteth-20.

Examples of suitable acrylate copolymers include, without limitation, those sold under the trademarks CARBOPOL® AQUA SF-1 from Noveon (Cleveland, Ohio), SYNTHALEN® W2000 from 3V (Wehawkin, N.J.), ACULYN® 22, and ACULYN® 33 available from International Specialty Products Corporation (Wayne, N.J.).

Suitable alkaline neutralizing agents include, without limitation, inorganic and organic neutralizers selected from the group consisting of alkali hydroxides (such as ammonium, sodium, and potassium) and alkanolamines (such as triethanolamine, isopropanolamines), preferably, sodium hydroxide or triethanolamine.

In certain embodiments, compositions of the invention may optionally comprise opacifying and/or suspending agents including, but not limited to: glycol stearates and glycol distearates, including, without limitation, ethylene glycol distearate, ethylene glycol monostearate and polyethylene glycol distearate; coated micas, glitter and mixtures thereof.

Compositions according to the invention may be made using conventional mixing techniques known to those skilled in the art for mixing ingredients.

EXAMPLES

The invention is further demonstrated in the following examples. The examples are for purposes of illustration and are not intended to limit the scope of the present invention. In the Examples, as elsewhere in this application, values for n, m, etc. in formulas, molecular weights and degree of ethoxylation or propoxylation are averages. Temperatures are in degrees C. unless otherwise indicated. The amounts of the components may be in weight percents based on the standard described; if no other standard is described then the total weight of the composition is to be inferred (active basis). Various names of chemical components include those listed in the *CTFA International Cosmetic Ingredient Dictionary* (Cosmetics, Toiletry and Fragrance Association, Inc., 7$^{th}$ ed. 1997).

General Method of Making Compositions

Using the types and amounts of ingredients listed in the examples, the products are prepared at ambient temperature (approximately 20-25 degrees C) by adding the DMDM Hydantoin to the water in a vessel equipped with center turbine agitation. The acrylate copolymer is then added to the water phase and mixed. The sodium laureth sulfate is added to the mixture and then neutralized with sodium hydroxide to a pH range of 6.5-7.5 at 25° C. Cocamidopropyl betaine is then added and mixed. The other ingredients are added in order and mixed until uniform. The citric acid is added to adjust the pH to approximately 6.4-7.2. The sodium chloride is added to adjust the viscosity to approximately 4300 centipoise (cps), wherein the formulation viscosity is in the range of 2500-5500 cps as measured by a Brookfield DV II+ Viscometer using Spindle # 5 at 20 RPM at 25° C.

Example 1

Pearlized Liquid Hand Soap with Glucams

TABLE 1

| INCI Name | Tradename | % (weight/weight) | % (weight/weight on an active basis) |
|---|---|---|---|
| Water | Water | 44.10 | 83.12 |
| DMDM Hydantoin | GLYDANT PLUS ® | 0.40 | 0.24 |
| Acrylate Copolymer (30%) | CARBOPOL ® AQUA SF-1 | 8.50 | 2.55 |
| Sodium Laureth Sulfate (25.5%) | STANDAPOL ® ES-2 | 35.22 | 8.98 |
| Sodium Hydroxide (50%) | Sodium Hydroxide | 0.70 | 0.35 |
| Cocamidopropyl Betaine (30%) | EMPIGEN ® BS/CQ | 5.35 | 1.61 |
| Tetrasodium EDTA (39%) | DISSOLVINE ® E-39 | 0.08 | 0.03 |
| Methyl Gluceth-10 | GLUCAM ™ E-10 | 0.50 | 0.50 |
| PPG-10 Methyl Glucose Ether | GLUCAM ™ P-10 | 0.30 | 0.30 |
| Glycol Distearate | EUPERLAN ® PK 3000 AM | 2.00 | 1.04 |
| Butyrospermum Parkii (Shea Butter), Gelatin, Acacia Senegal Gum, Iron Oxide | HC-1741 Beads | 0.50 | 0.50 |
| Fragrance | Skin Balm | 0.35 | 0.35 |
| Citric Acid (50% solution) | Citric Acid | 0.10 | 0.05 |
| Sodium Chloride (25% solution) | Sodium Chloride | 1.50 | 0.38 |
| Total weight | | 100.00 | 100.00 |

Example 2

Pearlized Liquid Hand Soap without Glucams

TABLE 2

| INCI Name | Tradename | % (Weight/weight) | % (Weight/weight on an active basis) |
|---|---|---|---|
| Water | Water | 44.90 | 83.92 |
| DMDM Hydantoin | GLYDANT PLUS ® | 0.40 | 0.24 |
| Acrylate Copolymer (30%) | CARBOPOL ® AQUA SF-1 | 8.50 | 2.55 |
| Sodium Laureth Sulfate (25.5%) | STANDAPOL ® ES-2 | 35.22 | 8.98 |
| Sodium Hydroxide (50%) | Sodium Hydroxide | 0.70 | 0.35 |
| Cocamidopropyl Betaine (30%) | EMPIGEN ® BS/CQ | 5.35 | 1.61 |
| Tetrasodium EDTA (39%) | DISSOLVINE ® E-39 | 0.08 | 0.03 |
| Methyl Gluceth-10 | GLUCAM ™ E-10 | 0.00 | 0.00 |
| PPG-10 Methyl Glucose Ether | GLUCAM ™ P-10 | 0.00 | 0.00 |
| Glycol Distearate | EUPERLAN ® PK 3000 AM | 2.00 | 1.04 |
| Butyrospermum Parkii (Shea Butter), Gelatin, Acacia Senegal Gum, Iron Oxide | HC-1741 Beads | 0.50 | 0.50 |

TABLE 2-continued

| INCI Name | Tradename | % (Weight/ weight) | % (Weight/ weight on an active basis) |
|---|---|---|---|
| Fragrance | Skin Balm | 0.35 | 0.35 |
| Citric Acid (50% solution) | Citric Acid | 0.10 | 0.05 |
| Sodium Chloride (25% solution) | Sodium Chloride | 1.50 | 0.38 |
| Total weight | | 100.00 | 100.00 |

Example 3

Clear Antibacterial Liquid Hand Soap

TABLE 3

| INCI Name | Tradename | % (Weight/ weight) | % (Weight/ weight on an active basis) |
|---|---|---|---|
| Water | Water | 44.18 | 83.00 |
| DMDM Hydantoin | GLYDANT PLUS ® | 0.42 | 0.25 |
| Acrylate Copolymer (30%) | CARBOPOL ® AQUA SF-1 | 8.74 | 2.62 |
| Sodium Laureth Sulfate (25.5%) | STANDAPOL ® ES-2 | 36.25 | 9.24 |
| Sodium Hydroxide (50%) | Sodium Hydroxide | 0.72 | 0.36 |
| Cocamidopropyl Betaine (30%) | EMPIGEN ® BS/CQ | 5.51 | 1.65 |
| Tetrasodium EDTA (39%) | DISSOLVINE ® E-39 | 0.21 | 0.08 |
| Methyl Gluceth-10 | GLUCAM ™ E-10 | 0.50 | 0.50 |
| PPG-10 Methyl Glucose Ether | GLUCAM ™ P-10 | 0.50 | 0.50 |
| Butyrospermum Parkii (Shea Butter), Gelatin, Acacia Senegal Gum, Iron Oxide | HC-2329 Beads | 0.50 | 0.50 |
| Triclosan | IRGASAN ® DP300 | 0.12 | 0.12 |
| Fragrance | Cosmolem | 0.35 | 0.35 |
| FD&C Colors | Color | 0.40 | 0.40 |
| Citric Acid (50% solution) | Citric Acid | 0.10 | 0.05 |
| Sodium Chloride (25% solution) | Sodium Chloride | 1.50 | 0.38 |
| Total weight | | 100.00 | 100.00 |

Example 4

Rheology Testing

Rheology of cleansing liquids is key to a consumer's perception of consistency and dispensing. Consumers perform flow experiments when they use the product. How a product flows in a bottle and is dispensed, how the product is pumped and dispensed and how the product is spread out in use to generate lather are all examples of a shear force being applied.

A series of rheological measurements including strain sweep and creep tests were conducted. All rheological measurements were conducted using a Paar Physical MCR300 Rheometer equipped with a TEK 150 P-CF peltier plate, a 50 mm parallel plate (PP50) and a 1 millimeter gap at 23° C.

Strain sweeps are used to define the linear viscoelastic (LVE) region and determine the magnitude of G' (elastic modulus) and G" (viscous modulus) of an intact substance and is expressed as tan (delta) which equals G" over G'. If tan (delta) is greater than 1.0, the substance is viscous dominant and if tan (delta) is smaller than 1.0, the substance is elastic dominant. Creep tests determine the relative contribution of the elastic and viscous elements.

Table 4: Key Rheological Parameter Results

TABLE 4

| Rheology Parameter | Pearlized Liquid Hand Soap with Glucams Example 1 | Pearlized Liquid Hand Soap without Glucams Example 2 |
|---|---|---|
| Elastic Portion, % | 45.3 | 23.3 |
| G' within LVE | 77.0 | 83.1 |
| G" within LVE | 29.6 | 38.0 |
| Tan (delta), G"/G' | 0.38 | 0.46 |
| Yield Value (Pa) | 3.6 | 4.2 |

The rheological measurements indicate that the Liquid Hand Soap with the Glucams has a higher elastic portion, a lower tan (delta) and a lower G". The greater the value of G" or tan (delta) the stringier the product, which is consistent with sensory evaluations and not as desirable.

Example 5

Sensory Panel—Hand Wash Dispensing Study

For evaluating aesthetic properties, a composition of Example 1 was compared on the basis of aesthetics for foaming and dispensing from a liquid hand soap container to the composition of Example 2.

Methodology:

Products:

Pearlized Liquid Hand Soap with Glucams (control) Example 1

Pearlized Liquid Hand Soap without Glucams Example 2

Procedure:

Two products were tested in two phases: a sequential monadic hand wash phase and a side-by-side dispensing phase.

Part 1—Hand Wash Evaluation: Each panelist washed with each product over 2 test sessions. Panelists dispensed the product using their normal habits, then washed their hands with the product (in water temperature about 37° C.+/−1° C.) and evaluated the product. Each panelist evaluated all products in a balanced/randomized order of presentation. Panelists answered a series of questions related to the dispensing and hand washing-properties of the product.

Part 2—Dispensing Evaluation: Upon completing the hand wash portion of the study, panelists evaluated the dispensing properties of the 2 products (randomized presentation). Panelists pumped each product twice into a dish to evaluate the dispensing properties. Panelists were instructed to pump as they would normally pump, wait for the pump to recover (count to 10) and then pump the product again. This procedure was repeated with each product. Panelists answered a series of questions related to the dispensing properties in between each product.

Subjects:
79 liquid hand soap users participated in the study.

Results of Comparison of Pearlized Liquid Hand Soap with Glucams Versus Without Glucams Part I: Hand Wash and Dispensing (see Table 6)
  Pearlized Liquid Hand Soap without Glucams was rated as having less lather compared to the Pearlized Liquid Hand Soap with Glucams.

Part II: Dispensing Only (see Table 5)
  The Pearlized Liquid Hand Soap without Glucams was rated as being more stringy as it was dispensed compared to the Pearlized Liquid Hand Soap with Glucams.

TABLE 5

Rate how stringy the product was as you dispensed it

| Rating | | Pearlized Liquid Hand Soap without Glucams N = 78 | Pearlized Liquid Hand Soap with Glucams N = 79 |
|---|---|---|---|
| Very Stringy | | % | % |
| 7 | | 1.3 | 1.3 |
| 6 | | 12.8 | 5.1 |
| 5 | | 16.7 | 9.0 |
| 4 | | 16.7 | 20.5 |
| 3 | | 20.5 | 19.2 |
| 2 | | 23.1 | 33.3 |
| 1 | | 9.0 | 11.5 |
| Not at all Stringy | Mean | 3.5 | 3.0 |

TABLE 6

Rate the Amount of Lather generated while washing

| Rating | | Pearlized Liquid Hand Soap without Glucams N = 78 | Pearlized Liquid Hand Soap with Glucams N = 79 |
|---|---|---|---|
| A Lot of Lather | | % | % |
| 7 | | 1.3 | 1.3 |
| 6 | | 6.4 | 15.2 |
| 5 | | 15.4 | 26.6 |
| 4 | | 24.4 | 25.3 |
| 3 | | 28.2 | 17.7 |
| 2 | | 12.8 | 8.9 |
| 1 | | 11.5 | 5.1 |
| Very Little Lather | Mean | 3.5 | 4.1 |

Example 6

Foam Evaluation Testing—Cylinder Shake Test

The foam characteristics of liquid hand soap products were evaluated using a mechanical cylinder shake method. The procedure uses hard water, synthetic sebum and a Gaum Foam Machine available from Gaum, Inc., Robbinsville, N.J.

Hard Water Preparation: In a 2000 milliliter volumetric flask combine 40 grams of magnesium chloride ( ) and 45 grams of calcium chloride and fill volumetric to line with deionized water. This will produce 25,000 ppm water hardness. To prepare 250 ppm hard water, put 20 milliliters of 25,000 ppm hard water solution into a 2000 milliliter volumetric flask and fill to the line with deionized water.

Synthetic Sebum Preparation:

The Synthetic Sebum was prepared by melting together the following ingredients at about 71° C. while stirring with a spatula.

| | % weight/weight |
|---|---|
| Palmitic Acid | 10.0 |
| Stearic Acid | 5.0 |
| Coconut Oil | 15.0 |
| Paraffin | 10.0 |
| Spermaceti | 15.0 |
| Olive Oil | 20.0 |
| Squalene | 5.00 |
| Cholesterol | 5.00 |
| Oleic Acid | 10.0 |
| Linoleic Acid | 5.0 |
| | 100.0 |

Foam height testing was performed on the compositions in Examples 1 and 2 above. 15 grams of liquid hand soap were added to 84 grams of 250 ppm hard water and 1 gram of Synthetic Sebum. The hard water was prepared by mixing together 40 grams of $MgCl_2.6H_2O$ with 45 grams of $CaCl_2.2H_2O$ and diluting to 250 ppm. The test mixture was then heated with moderate agitation and slow heating to 40.5° C. This dispersion was then carefully poured into a 600 ml. graduated cylinder containing a plastic water-filled tube. The cylinder was then mounted onto the center of a Vertical Rotator Assembly and rotated at a constant speed of 30 rpm. The action of the circular mixing of the cylinder and the free falling action of the water-filled tube in the cylinder generated foam which could be measured as foam height using the gradations on the side of the cylinder. After 8 complete revolutions, the Flash Foam Height was measured and after an additional 12 complete revolutions (a total of 20 revolutions) the Maximum Foam Height was measured. At this time the Drainage Time was also measured. Drainage Time is defined as the time measured from the completion of the 20 revolutions to the time at which 100 mls. of apparent liquid has drained. Drainage Time is a measure of the wetness and stability of the foam.

TABLE 7

Foam Evaluation Testing
1 gram Sebum
15 grams Liquid Soap
84 grams 250 PPM Water
At 40.5° C.

| Product Code | Flash Foam (ml) | Maximum Foam (ml) | Drainage Time (Min.Sec.) |
|---|---|---|---|
| Pearlized Liquid Hand Soap without Glucams | 325 | 400 | 5.77 |
| Pearlized Liquid Hand Soap with Glucams | 375 | 495 | 4.65 |

The results of foam evaluation testing indicate that the Pearlized liquid hand soap with Glucams had more flash foam and maximum foam height. The drainage time took less time and represents a more stable foam.

All numerical ranges described herein include all combinations and subcombinations of ranges and specific integers encompassed therein.

Various modifications of the invention, in addition to those described herein, will be apparent to those skilled in the art from the foregoing description. Such modifications are also intended to fall within the scope of the appended claims.

What is claimed:

1. A cleansing composition comprising an acrylate copolymer, an alkoxylated methyl glucoside ether in an amount of about 0.05 to 4% by weight of the total cleansing composition, and a surfactant comprising at least one surfactant chosen from anionic surfactants and amphoteric surfactants.

2. The composition of claim 1 further comprising a basic neutralizing agent.

3. The composition of claim 1 wherein the anionic surfactant is present in an amount of about 3% to about 25% by weight of the total composition.

4. The composition of claim 1 wherein the amphoteric surfactant is present in an amount of about 0.05% to about 15% by weight of the total composition.

5. The composition of claim 1 wherein the amphoteric surfactant is a betaine surfactant.

6. The composition of claim 1 wherein the amphoteric surfactant is selected from the group consisting of alkyl betaines, alkylamido betaines, alkyl sulfobetaines, alkyl sultaines, alkylamido sultaines, and mixtures thereof.

7. The composition of claim 1 wherein the amphoteric surfactant comprises alkyl and/or acyl groups having from about 8 to about 18 carbons.

8. The composition of claim 1 wherein the alkoxylated methyl glucoside ether is present in an amount of about 0.05% to about 2% by weight of the total composition.

9. The composition of claim 1 wherein the alkoxylated methyl glucoside ether is selected from the group consisting of ethoxylated methyl glucosides, propoxylated methyl glucosides, and mixtures thereof.

10. The composition of claim 9 wherein the alkoxylated methyl glucoside ether has an average degree of alkoxylation of about 8 to about 22.

11. The composition of claim 1 wherein the alkoxylated methyl glucoside ether is selected from the group consisting of methyl gluceth-10 methyl gluceth-20, PPG-10 methyl glucose ether, PPG-20 methyl glucose ether, and mixtures thereof.

12. The composition of claim 1 wherein the acrylate copolymer is present in an amount of about 0.1% to about 12% by weight of the total composition.

13. The composition of claim 2 wherein the basic neutralizing agent is present in an amount of about 0.01% to about 5% by weight of the total composition.

14. The composition of claim 1 further comprising effective amounts of one or more members selected from the group consisting of colorants, fragrances, antibacterial, preservatives, antioxidants, beads, mica, glitter, opacifying agents, and pearlizing agents.

15. The composition of claim 14 wherein the beads comprise members selected from the group consisting of fragrances, exfoliating agents, moisturizing agents, and mixtures thereof.

16. The composition of claim 14 wherein the beads comprise shea butter.

17. A cleansing composition comprising:
   (a) an anionic surfactant;
   (b) an amphoteric surfactant;
   (c) an acrylate copolymer;
   (d) an alkoxylated methyl glucoside ether in an amount of about 0.05 to 4% by weight of the total cleansing composition;
   (e) a basic neutralizing agent; and
   (f) water.

18. A cleansing composition comprising:
   a) about 3% to about 25% of an anionic surfactant;
   b) about 0.05% to about 15% of an amphoteric surfactant;
   c) about 0.1% to about 12% of an acrylate copolymer;
   d) about 0.05% to 4% of alkoxylated methyl glucoside ether;
   e) about 0.01% to about 5% a basic neutralizing agent; and
   water.

19. A method of making a cleansing composition comprising the steps of:
   a) mixing acrylate copolymer and water to form a water phase;
   b) adding an anionic surfactant to the water phase of step a) to form a mixture;
   c) adding a basic neutralizing agent to the mixture of step b) to form a neutralized material;
   d) mixing an amphoteric surfactant with the neutralized material of step c);
   e) adding an alkoxylated methyl glucoside ether in an amount of about 0.05 to 4% by weight of the total cleansing composition to the result of step d) to form a cleansing composition.

* * * * *